United States Patent [19]

Bouma et al.

[11] Patent Number: 5,208,350

[45] Date of Patent: May 4, 1993

[54] 7-HYDROXY COUMARINS HAVING SUBSTITUTIONS IN THE 4 POSITION

[75] Inventors: Stanley R. Bouma, Mundelein; Joseph E. Celebuski, Gurnee, both of Ill.

[73] Assignee: Abbott Laboratories, Abbott Park, Ill.

[21] Appl. No.: 705,709

Related U.S. Application Data

[63] Continuation-in-part of Ser. No. 394,052, Aug. 17, 1989, abandoned.

[22] Filed: May 21, 1991

[51] Int. Cl.$^5$ .............................................. C07D 311/16
[52] U.S. Cl. ..................................... 549/289; 549/214
[58] Field of Search ................................. 549/214, 289

[56] References Cited

U.S. PATENT DOCUMENTS 4,618,622 10/1986 Schlecker et al. .................. 514/457

OTHER PUBLICATIONS

Kato et al., CA 91:74247m.

*Primary Examiner*—Jane T. Fan
*Attorney, Agent, or Firm*—Thomas D. Brainard

[57] ABSTRACT

This invention relates to fluorescent 7-hydroxy coumarin compounds with substitutions in the 4 position having a length greater than one carbon atom. The compounds thus are related to 4-methylumbelliferone (7-hydroxy-4-methyl coumarin, or 4-MU), the detectable label used in the IM$_x$ ® instrument assays (Abbott Laboratories, Abbott Park, Ill.). The substitutions in the 4 position are branched and include functional groups for coupling to biological molecules.

13 Claims, No Drawings

7-HYDROXY COUMARINS HAVING SUBSTITUTIONS IN THE 4 POSITION

This application is a continuation-in-part of application Ser. No. 07/394,052 filed Aug. 17, 1989, hereby abandoned; the entire disclosure of which is incorporated herein by reference.

BACKGROUND OF THE INVENTION

This invention relates to fluorescent 7-hydroxy coumarin compounds with substitutions in the 4 position having a length greater than one carbon atom. The compounds thus are derivatives of 4-methylumbelliferone (7-hydroxy-4-methyl coumarin, or 4-MU), the detectable label used in the IM$_x$ ® instrument assays (Abbott Laboratories, Abbott Park, Ill.). The substitutions in the 4 position are branched and include functional groups for coupling to biological molecules.

A number of fluorometric labels are known to one of ordinary skill in the art. However, for compatibility reasons, applicants desired a fluorophore label that had electronic properties substantially similar to the 4-MU utilized in the IM$_x$ ® instrument. Otherwise, the label might fluoresce at a wavelength the instrument could not detect absent special filters and the like. A label optimized to the existing instrument was desired. The search began for a coumarin or umbelliferone nucleus that had an activated or activatable tether which could be coupled to a desired molecule. Of course, the tether had to be one which did not substantially alter the electronic properties of the coumarin nucleus.

A tether to a coumarin nucleus had been obtained in the past by a Pechmann condensation to give a 4-methyl group on the coumarin ring [H. V. Pechmann and C. Duisberg, Chem. Ber. 16, 2119 1883)]. Unfortunately, the 4-methyl compound does not provide useful functional groups which can serve to connect the label to a biological molecule.

A reaction very similar to the Pechmann condensation is described in U.S. Pat. No. 4,618,622 (Schlecker, et al.), whereby certain substituents are placed in the 3 or 4 positions of the coumarin ring by condensation of dihydroxybenzene with a β-ketocarboxylate as follows:

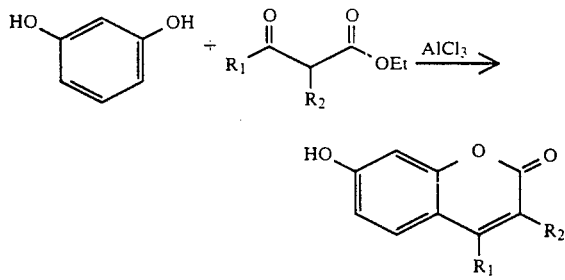

where R$_1$ and R$_2$ represent the added side chains. Although Schlecker describes a fairly broad group of possibilities for the side chains, only hydrogen, methyl and ethyl are enabled as possible R$_1$ side chains going into the 4 position of the coumarin nucleus (except for the 3,4 tetramethylene ring). None of the enabled compounds bears a functional group which can be used to tether the fluorophore to a biological molecule. The substituents which may be placed at the 3 ring position do not retain the electronic properties of the coumarin required for fluoresence with the IMx instrument.

The effect of 3-position substitution on electronic structure in coumarins is shown in the $^{13}$C NMR spectra compiled by Parmar and Boll [Mag. Res. Chem., 26, 430-433 (1988)]. If R of the product above is H, the $^{13}$C NMR chemical shift of C-3 is 110 ppm; while if R is CH$_2$COOEt, C-3 resonates at 115 ppm. This means that the relative electron density on C-3 has decreased upon alkyl substitution, disturbing the electronic structure of the coumarin nucleus.

Kato, et al., (CA91:74247m and J. Chem. Soc., Perkin Trans. 1(2): 525-528 (1979)) describe a method of forming several compounds, including double ring structures, using keten. Compound 7a is allegedly a 7-hydroxycoumarin with a 2-ethoxycarbonylethyl group attached in the 4 position. However, this conclusion is not supported by the NMR data given for this compound in the second column of page 527.

Thus, the previously known condensation methods were not useful because they do not produce 4-substituted materials with activated or activatable functional groups, and because substitutions at the 3-position did not retain the desired electronic properties. A compound having no substituent at the 3-position was desired because of the need for substantially similar electronic properties as 4-MU.

SUMMARY OF THE INVENTION

In one aspect, the invention relates to a compound of the formula:

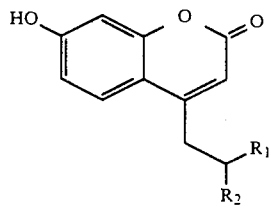

wherein R$_1$ is selected from the group consisting of —G—OZ, —G—SZ, —G—NHY, —OZ, —SZ, —NHY, and substituted or unsubstituted alkyl of the general formula —G—CH$_3$, where G represents an alkylene chain having from 1 to about 12 carbon atoms, and Z represents hydrogen or a protecting group for O or S, and Y represents hydrogen or a protecting group for N; and wherein R$_2$ is selected from the group consisting of —J—OH, —J—SH, —J—NHR′, —J—X, —SH, and —COOR′, where J represents an alkylene chain having from 1 to about 10 carbon atoms, X represents a halide, and R′ represents H or an alkyl chain having from 1 to about 10 carbon atoms.

In another aspect, the invention relates to a process of synthesis for the compounds described above. The steps of the synthesis comprise:

a) reacting 4-bromomethyl-7-methoxycoumarin with a monoalkylated (R$_1$) malonic ester under conditions sufficient to achieve condensation of the ester to give the monoalkylated (2-bis(carbalkoxy)-1-ethyl) derivative;

b) removing one of the carbalkoxy groups from the product of step a);

c) demethylation of the product of step b) to give the 7-hydroxycoumarin compound; and d) chemically modifying the remaining ester to yield a desired $R_2$ Preferably, step b) is performed according to the process of Krapcho in the presence of NaCl and DMSO at high temperatures. It is also preferred that step c) is performed by reacting ethanethiol (EtSH) with the product of step b) at 0° C. in the presence of $AlCl_3$ and dichloromethane.

Finally, the invention also comprises a method of using the compounds described above. The 7-hydroxy-4-methyl coumarins are known to fluoresce. By conjugating the compounds to a biological macromolecule, the presence or absence of the macromolecule can be quantified. For example, a method of using compounds as labels according to the invention comprises:

a) coupling the compound to a biological macromolecule to be used in a reaction of interest;

b) carrying out the reaction of interest; and c) determining the presence or amount of the macromolecule by measuring the fluorescence of the compound.

Preferably, the compounds according to the invention are conjugated to a member of a specific binding pair, such as an antibody or antigen for determination in an immunoassay. They may also be conjugated to oligonucleotides and used in hybridization assays, or amplification techniques such as LCR or PCR.

DETAILED DESCRIPTION OF THE INVENTION

The invention comprises compositions of matter, processes of synthesis and methods of use for the compounds.

Compounds

In one aspect, the invention relates to compounds having the general formula:

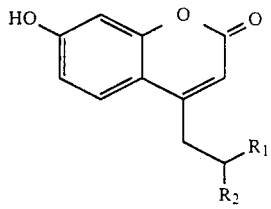

wherein $R_1$ is selected from the group consisting of —H, —G—OZ, —G—SZ, —G—NHY, —OZ, —SZ, —NHY, and substituted or unsubstituted alkyl of the general formula —G—CH_3, where G represents an alkylene chain having from 1 to about 12 carbon atoms, and Z represents hydrogen or a protecting group for O or S, and Y represents hydrogen or a protecting group for N; and wherein $R_2$ is selected from the group consisting of —J—OH, —J—SH, —J—NHR', —J—X, —SH, and —COOR', where J represents an alkylene chain having from 1 to about 10 carbon atoms, X represents a halide, and R' represents H or an alkyl chain having from 1 to about 10 carbon atoms.

Arbitrarily, $R_1$ derives from the central, monoalkylated $R_1$ of the malonic ester; while $R_2$ is converted from the COOEt end chain of the ester. $R_1$ can be selected from any of the groups listed above, although hydrogen, and alkyl, particularly lower alkyl, are preferred. Some $R_1$ groups may require protecting groups to enable them to withstand the ensuing reactions. As used herein, "protecting group" refers to any group that can be attached to a functional moiety permitting it to withstand future reaction conditions without destroying the function; and which later can be removed or substituted to give back the functional group. For example, if alcohol or thiol groups are used, a protecting group Z is used. In the case of alcohols, Z may be t-butyldimethylsilyl or tetrahydropyran; while for thiols, a preferred Z is triphenylmethyl. A single letter "Z" is used to designate protecting groups for both thiols and alcohols because many of the protecting groups will work for either. However, the invention is not limited to protecting groups which will protect both functionalities. Protecting group Y is similarly required for amino substituents. In this case, acetyl is a preferred protecting group. It is to be understood, of course, that other protecting groups are known in the art. See, e.g. Greene, *Protective Groups in Organic Synthesis* (J. Wiley & Sons, New York, N.Y. 1981), pp 295-331, wherein Reactivity Charts of numerous protecting groups are set forth and are incorporated herein by reference. Other protecting groups are obvious extensions falling within the scope of the invention.

$R_2$ can be a greater number of groups since it is converted from the COOEt ester after the other reactions are completed. Conventional organic chemistry methods can place almost any group in the $R_2$ position, although there is little practical reason why some groups would be made. The preferred group will be dictated by the linking moiety present on the biological macromolecule of interest (see below). For example, if the macromolecule contains a primary amine, it is preferred that $R_2$ be (or be converted to) a N-hydroxysuccinimide ester. Other preferred $R_2$ groups are given in Table 1 below. A tosyl group, Ts, may also be created at $R_2$ and is useful as an intermediate to create other $R_2$ groups as shown in the Examples. In many cases, a carboxyl group is preferred.

In general, terms like "alkyl", "alkenyl" and "aryl" have the meanings usually attributed to them by persons skilled in the art of organic chemistry. For example, alkyl refers to monovalent straight or branched aliphatic radicals which may be derived from alkanes by the removal of one hydrogen, and have the general formula $C_nH_{2n+1}$. Alkyl substituents may have from 1 to about 30 carbons, more practically 1 to about 20. "Lower alkyl" refers to alkyls having from 1 to about 6 carbons. Examples of lower alkyl include $CH_3$—, $CH_3CH_2$—, $CH_3CH(CH_3)$—, and $CH_3(CH_2)_4$—.

As used herein, "alkylene" refers to any straight or branched divalent spacer group containing less than 50 carbon atoms, including but not limited to, —$CH_2$—, —$CH(CH_3)$—, —$CH(C_2H_5)$—, —$CH(CH_3)CH_2$—, —$(CH_2)_3$—, and the like. The length of the alkylene chain is preferably short to enhance solubility, to avoid steric problems, and to be readily available commercially. Ideally, the alkylene chain G should be from 1 to about 5 or 6 carbon atoms long, while the alkylene chain J should be from 1 to about 5 carbon atoms long. In either case, the alkylene chain may be substituted.

"Aryl" refers to a monovalent radical derived from aromatic hydrocarbons by the removal of one hydrogen. Aryl substituents have ring structures, such as those of phenyl and naphthyl. Typically, aryl substituents are planar with the π electron clouds of each carbon remaining on opposite sides of the plane.

Both aryl and alkylene substituents at the $R_1$ position may be substituted. As used herein, "substituted" refers to the presence of moieties covalently bonded to the aryl or alkylene groups, including, but not limited to, halide (especially Br and Cl), nitro, lower alkoxy (having from 1-6 carbon atoms, especially methoxy and ethoxy), lower alkyl (having from 1-6 carbon atoms, especially methyl and ethyl), hydroxy, and amino (protecting group may be required). Subject to the limits of organic chemistry, the substituting groups may be placed anywhere, and in any number, on the alkylene or phenyl substituent.

When $R_2$ is —COOR' or —J—NHR',R' may be H or lower alkyl. A preferred $R_2$ is the carboxylic acid, i.e. when R' is H.

It should be recalled that the object of the invention was to put an activated or activatable tether group in the 4 position of the coumarin nucleus. Therefore, if $R_1$ is alkyl, it would be pointless to convert $R_2$ to alkyl since there would then be no functional group to serve as a tether. It is important to the invention that at least one of $R_1$ and $R_2$ provide a functional group that is, or can be activated to be, reactive with a biological macromolecule or a linker as described below.

The compounds of the present invention find utility as fluorophores. Specifically, the side chains in the 4 position enable the compounds to be covalently coupled to other molecules through conventional chemistries, without affecting the electron configurations that are responsible for their fluorometric properties. For example, the 7-hydroxy-2-oxo-2H-1-benzopyran-4-propionic acid was synthesized for the purpose of covalently labeling biological macromolecules such as oligonucleotide primers. An example of how the compounds are so used can be found in copending application Ser. No. 07/394,051, which is incorporated herein by reference. The labeled macromolecules can then be detected by any fluorometric procedure, such as on an $IM_x$ ® instrument, without recourse to enzymatic signal amplification.

The compounds can also be used as dye markers at the 5' end of an oligonucleotide for sequencing purposes.

Process of Synthesis

The compounds of the present invention can be chemically synthesized in 3 or more steps starting from 4-bromomethyl-7-methoxycoumarin 1 (Aldrich Chemical Co., Milwaukee, Wis.). The compounds were prepared as shown below. Generally speaking, malonic ester displacement of the bromide in 1, in the presence of NaH, afforded monoalkylated 2 according to the following reaction:

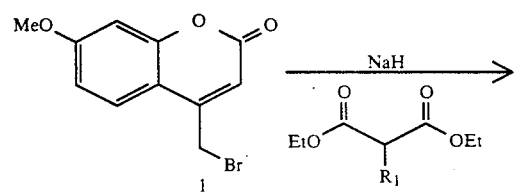

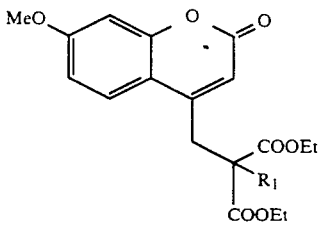

Krapcho decarbalkoxylation [Krapcho, A. P.; Weimaster, J. F.; Eldridge, J. M.; Jahngen, Jr., E. G. E.; Lovey, A. J.; Stephens, W. D. *J. Org. Chem.* (1978) 43: 138–147] removed one of the two ester groups to give 3 in good yield. The reaction is best carried out at high temperatures using NaCl as follows:

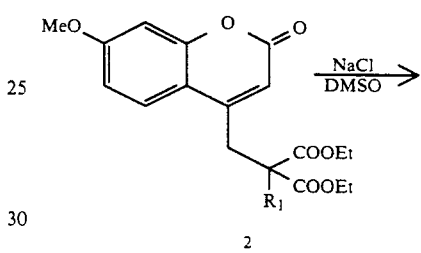

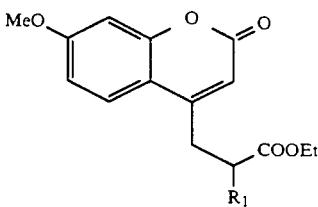

Demethylation of 3 to give the 7-hydroxycoumarin was accomplished under the conditions of Fujita as described in [Node, et al *J. Org. Chem.* (1980) 45: 4275–4277]. Briefly, the conditions involve a strong Lewis acid, $AlCl_3$, and ethane thiol (EtSH) as a weak Lewis base, a source of protons, and a soft nucleophile. After several other methods (including $BBr_3$, [McOmie, et al. *Tetrahedron* (1968) 24: 2289–2292]; $Me_3Si$, [Ho, et al, *Angew. Chem.* (1976) 88: 847]; and NaSEt [Feutrill, et al, *Tetrahedron Letters* (1970) 161: 327–328]) failed, the conditions of Fujita finally effected demethylation to give 4, albeit in disappointing yields.

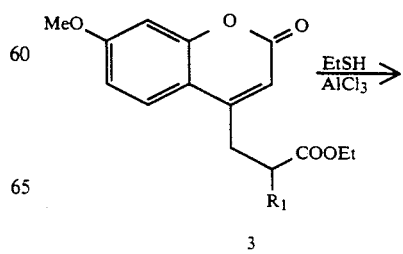

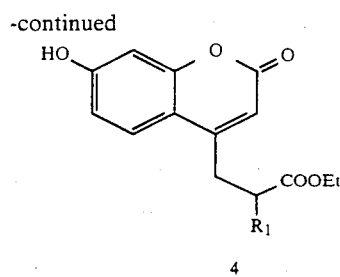

The ester is among the claimed $R_2$ groups. To arrive at the other $R_2$ groups, conventional organic chemistry can be used, directly from the ester or from other intermediate groups. For example, saponification of 4 gave the acid 5 as shown below.

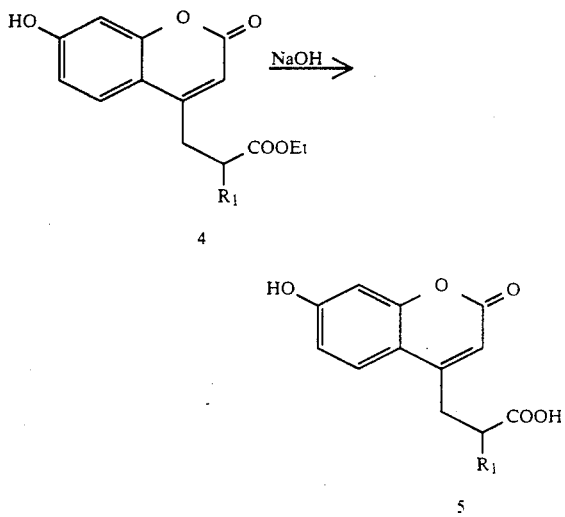

From either the ester or the acid, the remaining $R_2$ groups can be obtained through the following reactions. Where $R_2$ is to be an alcohol, $LiBH_4$ reduction gives the desired product. The alcohol hydroxyl can then be converted to either the thiol or the amino through the intermediate hydroxy tosylate. The ester may also be reduced to the aldehyde using diisobutylaluminum hydride (DIBAL, Aldrich Chemical Co.). Longer alkylene chains can be synthesized from the aldehyde using an appropriate Wittig or Wadsworth/Emmons reagent.

Methods of Use

Finally, the invention also comprises a method of using the compounds described above. The 7-hydroxy-4-methyl coumarins are known to fluoresce. By conjugating the compounds to a biological macromolecule, the presence or absence of the macromolecule can be quantified. For example, compounds according to the invention may be conjugated to antibodies for determination in an immunoassay. They may also be conjugated to oligonucleotides and used in PCR or other nucleic acid hybridization assays.

The conjugation is generally carried out by activating the fluorophore with a reactive group. In the case of a carboxyl $R_2$ to be reacted with a primary amine on a target macromolecule, the preferred activator is N-hydroxysuccinimide ester. Other activating groups are known in the art for use with the various $R_2$ groups and various target macromolecule linking moieties. Table 1 below is a nonexhaustive listing of some exemplary target moieties, likely $R_2$ groups and useful activators.

In some cases, the conjugation is best performed using a linker or spacer molecule. The linker may be heterobifunctional or homobifunctional depending on the circumstances. The correct linker can also be determined by one of ordinary skill in the art.

TABLE 1

| Target Moiety (on biomolecule) | Linker | Preferred Ultimate $R_1$ or $R_2$ Group | Activator |
| --- | --- | --- | --- |
| amine | none | carboxyl | NHS-ester |
| amine | maleimide | thiol | none (stable linkage) |
| amine | thiol | thiol | none (easily reversible linkage) |
| carboxyl | none | amine | (carbodiimide) |
| vicinal diol | (oxidation) | amine | (cyanoborohydride reduction after linkage) |
| thiol | none | amine | maleimide (stable linkage) |
| thiol | none | thiol | none (easily reversible linkage) |
| hydroxyl | (convert to tosyl) | amine | none |
| hydroxyl | (convert to phosphate ester) | hydroxyl | none |

The invention will now be further described by way of Examples.

EXAMPLES

EXAMPLE 1

Synthesis of 4-(2-carboxy-1-ethyl)-7-hydroxy-2-oxo-2H-1-Benzopyran

Throughout this example, $R_1$ represents Hydrogen.

A. Materials and Methods

Chemical reagents were purchased from Aldrich. Proton NMR spectra were obtained at 300 MHz on a General Electric QE-300 spectrometer, referenced to TMS internal standard in ppm (d). Coupling constants are given in hertz. Mass Spectra were obtained using direct chemical ionization on a Kratos MS 50 instrument. Aminomodifier II was purchased from Clontech Laboratories (Palo Alto, Calif.). TLC analyses were done using 250 μm Analtech silica gel plates. Flash column chromatographies were run with EM Kieselgel-60 (70–230 mesh). Spectral and elemental analyses were performed by the Analytical Research Department, Abbott Laboratories.

B. Synthesis of 4-(2-bis(carbethoxy)-1-ethyl)-7-methoxy-2-oxo-2H-1-Benzopyran (2)

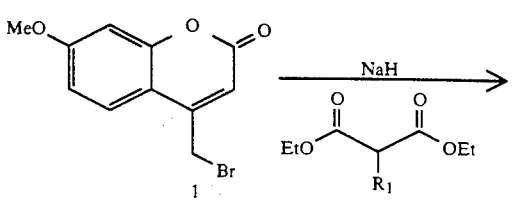

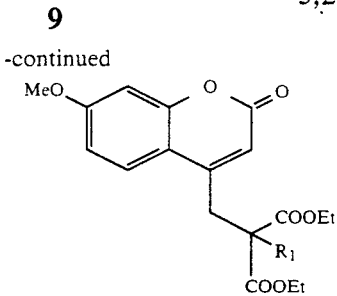

2

To a suspension of 240 mg of 60% NaH mineral oil dispersion (6 mmol) in 10 mL of DMF was added 961 μL (6 mmol) of diethyl malonate. After the foaming subsided and the suspension cleared to a solution, 1346 mg (5 mmol) of 4-bromomethyl-7-methoxycoumarin was added all at once. After stirring for 4 h at room temperature, the DMF was stripped off, and the residue partitioned between 0.01M HCl/hexane. The organic phase was concentrated and vacuum dried, then as much as possible was taken up into 4 mL of 50/50 EtOAc/hexane. Flash chromatography gave 670 mg of 2 as a white solid, 49%.

Analysis gave:

1H NMR (CDCl$_3$) d 7.56 (d, 1H, J=8.8), 6.88 (dd, 1H, J=2.6, 8.8), 6.84 (br s, 1H), 4.23 (q, 2H, J=7.2) 4.22 (q, 2H, J=7.2), 3.88 (s, 3H), 3.74 (t, 1H, J=7.4), 3.36 (dd, 2H, J=1.1, 7.4), 1.27 (t, 6H, J=7.4)

MS m/z 349 (100, M+H)

IR (film, cm−1) 1715 (vs), 1614 (vs)

Anal. (C$_{18}$H$_{20}$O$_7$) C, H.

C. Synthesis of 4-(2-Carbethoxy-1-ethyl)-7-methoxy-2-oxo-2H-1-Benzopyran (3)

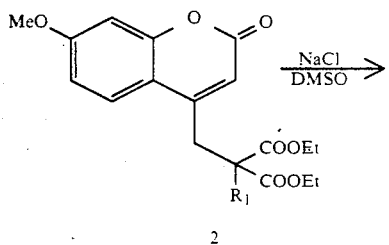

To a solution of 44.8 mg (0.13 mmol) of 2 in 6 mL of DMSO was added 15 mg of NaCl, followed by 4.6 mL of water. The reaction was stirred in an oil bath at 180° C. for 2.5 h, and was cooled to room temperature. After addition of 45 mL of water to the reaction mixture, the resultant emulsion was extracted with 2×40 mL EtOAc. The organic phase was concentrated by rotary evaporation, and was vacuum dried. After uptake into 3 mL of 25% EtOAc in hexane, flash chromatography using the same solvent system gave 31.4 mg of 3, 88%.

Analysis gave:

1H NMR (CDCl$_3$) d 7.55 (d, 1H, J=8.8), 6.88 (dd, 1H, J=2.6, 8.8), 6.83 (d, 1H, J=2.6), 6.13 (t, 1H, J=1.1), 4.19 (q, 2H, J=7), 3.88 (s, 3H), 3.06 (t, 2H, J=8), 2.71 (t, 2H, J=8), 1.28 (t, 3H, J=7)

MS 277 (100, M+H)

IR (film, cm−1) 1730(vs), 1612(vs)

Anal. (C$_{15}$H$_{16}$O$_5$) C, H.

D. Synthesis of 4-(2-carbethoxy-1-ethyl)-7-hydroxy-2-oxo-2H-1-Benzopyran (4)

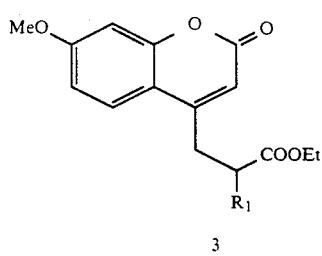

To a suspension of 726 mg (5.4 mmol) of AlCl$_3$ in 10 mL of dichloromethane at 0° C. was added 4 mL of EtSH. The suspension became a clear solution within seconds. Then, 298 mg (1.08 mmol) of 3 in 4 mL of dichloromethane was added, turning the yellow solution red in color. The ice bath was removed, and the reaction stirred to room temperature for 3 h. The solvents were removed in vacuo, and the residue thoroughly vacuum dried. The residue was extracted into EtOAc as much as possible, then the extract was flash chromatographed using 30/70 EtOAc/hexane. The long- and short-wave UV active band gave 76.7 mg (27%) of 4.

Analysis gave:

1H NMR (CDCl$_3$) d 7.5 (d, 1H, J=8.5), 6.9 (d, 1H, J=2.6), 6.85 (dd, 1H, J=8.5, 2.6), 6.1 (br s, 1H, 4.18 (q, 2H, J=7.4), 3.08 (br t, 2H, J=7), 2.71 (br t, 2H, J=7), 1.28 (t, 3H, J=7.4)

MS 263 (M+H)

IR (film, cm−1) 3280 (s, br), 1730 (vs), 1693 (vs), 1608 (vs), 1565 (s)

Anal. (C$_{14}$H$_{14}$O$_5$) C,H.

E. Synthesis of 4-(2-carboxy-1-ethyl)-7-hydroxy-2-oxo-2H-1-Benzopyran (5)

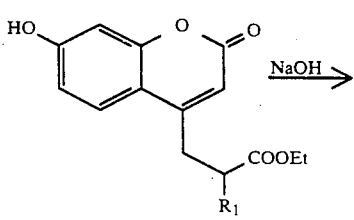

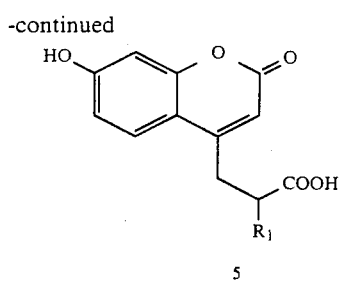

A 36.7 mg sample of ester 4 was suspended into 10 mL of water, and 25 uL of 50% aqueous NaOH was added. The resultant solution was stirred at room temperature for 4 h. TLC analysis (30/70 EtOAc/hexane) after this time showed that no starting material remained. The mixture was acidified using 1 mL of 1M HCl. A precipitate formed upon acidification, and the white solid was left to deposit for 1 h. After the solid was filtered off and thoroughly washed with 1M HCl, it was vacuum dried to give 14.1 mg (43%) of analytically pure 5.

Analysis gave:

1H NMR (NaOD/D$_2$O) d 7.5 (d, 1H, J=8.8), 6.74 (dd, 1H, J=2.2, 8.8), 6.53 (d, 1H, J=2.2), 5.97 (br s, 1H), 2.91 (t, 2H, J=7.4), 2.5 (t, 2H, J=7.4)

MS (FAB, H$_2$O) 235 (M+H)

IR (KBr, cm−1) 3440 (s, br), 1710 (vs), 1611 (vs), 1568 (vs), 1400 (s)

Anal. (C$_{12}$H$_{10}$O$_5$) C, H.

F. Synthesis of 4-(2-carboxy-1-ethyl)-7-hydroxy-2-oxo-2H-1-Benzopyran, N-hydroxy succinimide ester (6).

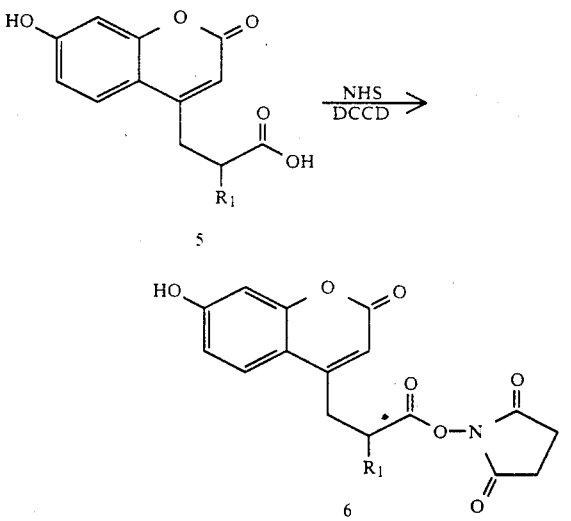

To a suspension of 6.4 mg (27.3 mmol) of 5 in 6 mL of MeCN was added 4.7 mg (41 mmol) of N-hydroxysuccinimide, 8.4 mg (41 mmol) of dicyclohexylcarbodiimide (DCCD) and 2 mg of 4,4-dimethylaminopyridine. The reaction was stirred at room temperature for 24 h, and the solvent was removed in vacuo. The residue was taken up into 750 μL of DMF, and coupled directly with oligonucleotide.

The coupling and use of this product are described in more detail in copending application Ser. No. 07/394,051, which has been incorporated herein by reference.

EXAMPLE 2

Synthesis of 4-(2-carboxy-2-R$_1$-1-ethyl)-7-hydroxy-2-oxo-2H-1-Benzopyran (R$_1$ is alkyl)

Example 1 is repeated with R$_1$ groups according to Table 2.

TABLE 2

| R$_1$ group |
|---|
| —CH$_3$ |
| —CH$_2$CH$_3$ |
| —(CH$_2$)$_2$CH$_3$ |
| —(CH$_2$)$_3$CH$_3$ |
| —CH(CH$_3$)$_2$ |
| —CH$_2$CH(CH$_3$)$_2$ |

EXAMPLE 3

Synthesis of Alcoholic R$_2$ Group

Compound (4) from Example 1 is modified to contain an alcoholic R$_2$ group (—CH$_2$OH) by reducing the ester with LiBH$_4$ under conditions cited by Brown in: H. C. Brown, Hydroboration, p. 245, Benjamin, N.Y., N.Y. (1962).

EXAMPLE 4

Synthesis of Thiol R$_2$ Group

The compound from Example 3 is modified to contain a thiol R$_2$ group (—CH$_2$SH) by conversion using the tosylate under conditions of Price and Stacy in: Organic Synthesis Collective vol. 3, p. 86 (1955).

EXAMPLE 5

Synthesis of Amine R$_2$ Group

The compound from Example 3 is modified to contain an amino R$_2$ group (—CH$_2$NH$_2$) by conversion using the tosylate under conditions of a Gabriel synthesis of primary amines, wherein the tosylate is displaced by sodium phthalimide. The phthalimide is then removed with hydrazine to give the primary amine.

EXAMPLE 6

Synthesis of 4-(2-carboxy-2-R$_1$-1-ethyl)-7-hydroxy-2-oxo-2H-1-Benzopyran (R$_1$ is protected)

Example 1 is repeated using R$_1$ groups on the malonic ester according to the first column of Table 6.

The compounds are then reacted under conditions such that the protecting groups are removed and replaced by hydrogen to give the compounds of the second column of Table 6. The —COOEt group may be converted to any desired R$_2$ as described in Examples 3-5.

TABLE 6

| Malonic Ester R$_1$ group | Coumarin substituent at 4 position |
|---|---|
| —CH$_2$CH$_2$—O-t-butyldimethylsilyl | —CH$_2$CH(COOEt)—CH$_2$CH$_2$—OH |
| —CH$_2$CH$_2$—O-tetrahydropyran | —CH$_2$CH(COOEt)—CH$_2$CH$_2$—OH |
| —CH$_2$CH$_2$—NH-acetyl | —CH$_2$CH(COOEt)—CH$_2$CH$_2$—NH$_2$ |
| —NH-acetyl | —CH$_2$CH(COOEt)—NH$_2$ |

TABLE 6-continued

| Malonic Ester R₁ group | Coumarin substituent at 4 position |
| --- | --- |
| —CH₂CH₂—S-diphenylmethyl | —CH₂CH(COOEt)—CH₂CH₂—SH |

The above examples serve to illustrate the invention and should not be construed as limiting the scope of the invention. Rather, the scope of the invention is limited only by the appended claims.

What is claimed is:

1. A compound of the formula:

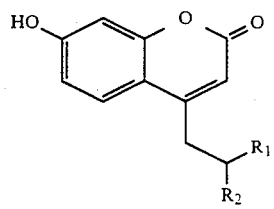

wherein $R_1$ is selected from the group consisting of —CH₃, —G—OZ, —G—SZ, —G—NHY, —OZ, —SZ, —NHY, and alkyl of the formula —G—CH₃, where G represents an alkylene chain having from 1 to 12 carbon atoms, and Z represents hydrogen or a protecting group for O or S, and Y represents hydrogen or a protecting group for N; and wherein $R_2$ is selected from the group consisting of —J—SH, —J—X, —OH, —SH, and —COOR', where J represents an alkylene chain having from 1 to 10 carbon atoms, X represents a halogen, and R' represents H or an alkyl chain having from 1 to 10 carbon atoms.

2. A compound according to claim 1, wherein Z is selected from t-butyldimethylsilyl, tetrahydropyran, and triphenylmethyl.

3. A compound according to claim 1, wherein Z is hydrogen.

4. A compound according to claim 1, wherein Y is acetyl.

5. A compound according to claim 1, wherein Y is hydrogen.

6. A compound according to claim 1, wherein G is an alkylene chain having from 1 to 5 carbon atoms.

7. A compound according to claim 1, wherein J is an alkylene chain having from 1 to 5 carbon atoms.

8. A compound according to claim 1 wherein $R_2$ is selected from the group consisting of —J—SH, —J—X, —OH, —SH, and —COOR', where J represents an alkylene chain having from 1 to 3 carbon atoms, X represents a halogen, and R' represents hydrogen or an alkyl chain having from 1 to 3 carbon atoms.

9. A compound according to claim 1 wherein $R_2$ is COOH.

10. A compound according to claim 1 wherein $R_1$ is lower alkyl.

11. A compound according to claim 1 wherein $R_1$ is selected from the group consisting of methyl, ethyl, n-propyl, and isopropyl.

12. A compound according to claim 10 wherein $R_2$ is selected from the group consisting of —J—SH, —J—X, —OH, —SH and —COOR', where J represents an alkylene chain having from 1 to 3 carbon atoms, X represents a halogen, and R' represents hydrogen or an alkyl chain having from 1 to 3 carbon atoms.

13. A compound according to claim 12 where $R_2$ is —COOR', where R' represents hydrogen or an alkyl chain having from 1 to 3 carbon atoms.

* * * * *